United States Patent [19]

Hoff et al.

[11] Patent Number: 4,868,237

[45] Date of Patent: Sep. 19, 1989

[54] MECHANICALLY DISRUPTIBLE BONE CEMENT

[75] Inventors: Günter Hoff, Daisendorf; Jochen Ohnsorge, Aachen, both of Fed. Rep. of Germany

[73] Assignee: Merck Patent Gesellschaft mit Beschränkter Haftung, Darmstadt, Fed. Rep. of Germany

[21] Appl. No.: 887,157

[22] PCT Filed: Oct. 24, 1985

[86] PCT No.: PCT/EP85/00561

§ 371 Date: Jun. 27, 1986

§ 102(e) Date: Jun. 27, 1986

[87] PCT Pub. No.: WO86/02560

PCT Pub. Date: May 9, 1986

[30] Foreign Application Priority Data

Oct. 29, 1984 [DE] Fed. Rep. of Germany ....... 3439533

[51] Int. Cl.⁴ .............................. C08K 3/10

[52] U.S. Cl. ...................... 524/407; 524/408; 524/430; 524/437

[58] Field of Search ............... 523/116; 524/430, 437, 524/407, 408

[56] References Cited

U.S. PATENT DOCUMENTS 4,341,691  7/1982  Anuta ................... 523/116
4,456,711  6/1984  Pietsch et al. ........ 524/560
4,490,497  12/1984 Evrard et al. ......... 523/116

Primary Examiner—Joseph L. Schoefer
Assistant Examiner—J. M. Reddick
Attorney, Agent, or Firm—Millen & White

[57] ABSTRACT

The invention relates to a bone cement based on physiologically tolerated polymers, the incorporation of acoustic perturbation elements having a sound resistance differing from that of the polymer making it possible, in the case of a necessary re-operation, to disrupt the bone cement by the application of acoustic waves to such an extent that it can easily be removed from the implant location.

16 Claims, No Drawings

MECHANICALLY DISRUPTIBLE BONE CEMENT

BACKGROUND OF THE INVENTION

The invention relates to a bone cement based on physiologically tolerated polymers, in particular on polyacrylates and/or polymethacrylates prepared from prepolymers and monomers, and to a process for mechanically disrupting fully polymerized plastics, in particular these bone cements.

A central problem in the implantation of joint endoprostheses is the anchorage of the prosthesis in the bone substrate. For this purpose, it is known to use bone cements which are based on acrylate and which are prepared by mixing and fully polymerizing pulverulent prepolymers with liquid monomers containing initiators and accelerators for the polymerization. These are used in orthopaedic surgery for the reliable and rapid primary fixing of the joint implant to the bone, thus enabling the patient to put a load on the joint at an early stage. The bone cement, which initially is still pasty in the mixing phase and cures slowly, fills the space between the bone and the joint implant almost without any gaps, but very rapidly gains its full strength as a result of the continuing polymerization process.

This type of fixing joint endoprostheses to the bone by means of fully polymerized bone cement is nowadays a surgical technique which is used and recognized throughout the world in orthopaedic surgery. Problems such as excessive liberation of energy and hence an unduly high temperature during the polymerization, whch leads to necrotization of the tissue, have been solved in principle, as have the questions of adequate biocampatibility of the bone cement.

In the long term, however, loosening of the metal implant or of the plastic implant in the bone cement substrate can occur, so that prosthesis replacements with removal of the bone cement become necessary. The removal of the bone cement from tubular bones is technically very difficult and involves a long operating time in the case of re-operations of joint endoprostheses, so that the predominantly old patients are put at considerable risk by long operating times, long bleeding times of the exposed soft tissues and an increased danger of infection due to long times with an open wound. The importance of this problem can be gauged by the fact that up to 20% of all joint prosthesis operations carried out nowadays are re-operations.

SUMMARY OF THE INVENTION

It was therefore the object to provide a bone cement which meets all the requirements with respect to stability and processability, but which can easily and quickly by removed from the bone in the case that a re-operation becomes necessary.

This object has been achieved by the present invention. In fact, it has been found that perturbation elements which have been incorporated into the polymer matrix and the acoustic resistance of which differs from that of the polymer matrix can be excited by means of acoustic waves in such a way that tensile and compressive stresses, which lead to disintegration of the polymer matrix, are generated at the acoustic interfaces.

The invention therefore relates to a bone cement based on physiologically tolerated polymers, in particular on polyacrylates and/or polymethacrylates prepared from prepolymers and monomers, wherein acoustic perturbation elements having an acoustic resistance differing from that of the polymer are incorporated into the polymer.

The invention also relates to a process for mechanically disrupting fully polymerized plastics, in particular bone cements based on physiologically tolerated polymers, in particular on polyacrylates and/or polymethacrylates prepared from prepolymers and monomers, which comprises incorporating acoustic perturbation elements having an acoustic resistance differing from that of the polymer, before the polymer is fully cured, and destroying the polymer matrix by selective excitation of the perturbation elements by means of acoustic waves.

The advantage of the present invention is that the bone cement according to the invention can be used by the surgeon in the same way as the hitherto known bone cements. With respect to short-term and long-term stability, the incorporation of the perturbation elements does not lead to any significant deterioration. An advantageous effect with respect to the stability of the bone cement is obtained when the perturbation elements are as similar as possible to the polymer with regard to the quasi-static mechanical properties, that is to say the parameters such as, for example, elasticity and compressibility which determine the stresses arising under normal loading (walking, running). Especially, however, when these properties differ, it is advantageous when the perturbation elements do not possess any sharp edges or points which can lead to undesired local stress concentrations and hence to cracks forming in the polymer matrix. Perturbation elements with rounded corners and edges, such as, for example, ellipsoids of revolution, cylindrical discs with rounded edges, or spheres, are therefore preferred.

In place of individual particles, however, it is also possible to use perturbation elements in the form of threads, braidings, fabrics, foils or plates. A nettype fabric, for example, can be used to particular advantage, since in this way, on the one hand, a considerable stabilization of the bone cement can be achieved and, on the other hand, in the case of a re-operation, the cement can be very effectively detached along the bone/cement contact layer, if the net is arranged in this boundary region.

The size and shape of the perturbation elements should be such that, on the one hand, optimum energy absorption from the extracorporeally generated acoustic waves is possible and that, on the other hand, there is no substantial interference with the processing of the bone cement. Perturbation elements of a size or thickness of about 0.01 to 2 mm, in particular a thickness of about 0.1 to about 1 mm, are therefore preferred.

In order to obtain effective disruption, a large number of perturbation elements, distributed as homogeneously as possible in the polymer matrix, is of course necessary. The more perturbation elements ae present, the more effective is the disruption. On the other hand, an excessive content of perturbation elements impairs the mechanical properties of the bone cement. A content of about 0.5 to about 20% by volume, in particular of about 3 to about 10% by volume, is therefore preferred.

The material used for the perturbation elements is a biocompatible material of which the acoustic resistance, that is to say the product of density and sound velocity, differs markedly from that of the polymer matrix. In particular, materials are used of which the acoustic resistance differs from that of the polymer by a factor of at least 1.5, preferably a factor of at least 1–10. The acoustic resistance of the perturbation elements can here by either greater or smaller than that of the polymer. Materials which can be used are therefore either bodytolerated metals or alloys, such as, for example, $TiAl_5Fe_{2.5}$, CoCrMo or tantalum, or oxidic materials, in particular in the form of burned oxide ceramics such as, for example, $Al_2O_3$, or glass or carbon. In place of these dense perturbation elements, however, it is also possible to use perturbation elements of a very low density, such as, for example, air bubbles or gas bubbles, which can be stirred in during mixing of the cement in a homogeneous distribution, or which can be liberated from suitable substances, for example by thermal decomposition during setting of the cement.

In order to obtain the greatest possible disruption of the bone cement throughout its entire volume, if individual particles are used, these perturbation elements should be distributed as homogeneously as possible in the bone cement. In the case of very heavy, especially metallic perturbation elements, it can therefore by advantageous to embed them in an envelope of polymer, in order to improve the dispersibility and to reduce sedimentation.

The bone cement according to the invention is prepared analogously to the known bone cements. These are prepared in such a way that approximately two parts of a finely particulate prepolymer containing a polymerization catalyst (for example dibenzoyl peroxide), in particular polymethyl methacrylate or a copolymer of methyl acrylate and methyl methacrylate, are mixed with approximately one part of the liquid monomer, for example methyl acrylate or methacrylate or mixtures thereof, containing an accelerator (for example dimethyl-p-toluidine), to give a formable composition which is implanted into the body and cures therein. Such bone cements are commercially available, for example under the trade mark Palacos ®. In addition, pharmacologically active substances such as, for example, antibiotics or materials which facilitate anchorage of the bone cement in the body such as, for example, absorbable tricalciumphosphate can also be incorporated therein. To prepare the bone cement according to the invention, the required quantity of perturbation elements is additionally incorporated into such a known bone cement.

In processing and also in the mechanical properties obtained after curing, the bone cement according to the invention is equivalent to the known bone cements. The advantage manifests itself, however, when a re-operation should become necessary. In this case, tensile and compressive stresses, which lead to breaking of the bond and to disintegration of the polymer matrix, can be generated according to the invention by means of extracorporeal acoustic waves at the acoustic interfaces between the perturbation elements and the polymer matrix.

The acoustic waves used here can be either shock waves generated extracorporeally and focused upon the bone cement plug or ultrasonic waves having a frequency tuned to the characteristic frequency of the perturbation elements.

Shock waves are already used in medical therapy for the crushing of urinary stones. The equipment used in this case for generating and focusing the shock waves can in principle also be used for the disruption of the bone cements according to the invention. By this means, shock waves in the pressure range from about 0.2 to about 5 kbar, in particular from about 0.5 to about 2 kbar, are generated. The profile of these shock waves, which have half widths of about $10^{-8}$ to about $10^{-6}$ seconds, is matched to the geometry of the perturbation elements in such a way that the half width of the shock wave is smaller than the thickness of the perturbation element and the pressure rise time is smaller than the half width by a factor of about 10. Preferably, shock waves of square profile which have pressure rise times of less than $10^{-7}$ seconds are used.

In contrast to the equipment used for the crushing of urinary stones, no involved and expensive stereo radiographic location systems and patient-positioning systems are required for the disruption of the bone cement according to the invention; instead, an optical-mechanical positioning system is provided for the task according to the invention. Using the X-ray and ultrasonic diagnostic equipment available in orthopaedic hospitals, the position of the bone cement plug in the tubular bone is determined and marked on the skin surface. The volumes to be swept by the focal point of the shock waves are unambiguously fixed geometrically relative to the skin surface by means of a measurement of the thickness of the connective tissue and bone tissue between the skin surface and the bone cement around the entire circumference of the joint endoprosthesis. By means of an optical system which is either integrated into the shock wave-generating system or is rigidly connected thereto on an adjustment rail, the focal point of the shock wave can be positioned exactly onto the bone cement which is to be destroyed.

A likewise inexpensive alternative to the optical-mechanical positioning system is an ultrasonic location system integrated into the shock wave generator.

An extracorporeal shock wave treatment of the bone cement of a patient just before the re-operation of his implant guarantees easy and reliable removal of the bone cement.

In place of shock waves, however, sonic waves in the ultrasonic region, that is to say in the MHz frequency range, can also be used. The ultrasonic frequency must be tuned to the characteristic frequency of the acoustic perturbation elements. The disruption of the bone cement proceeds via resonance effect of the perturbation elements. As a rule, frequencies from about 1 to 100 MHz are used, with an amplitude from about 0.1 to 10 bar.

The use of ulatrasonics has the advantage that ultrasonic equipment is very much less expensive than shock wave equipment. Electrodes as an expensive consumable material are completely absent, and the pressure amplitudes are smaller by a factor of about 1,000. Moreover, the ultrasonic equipment for the destruction of the bone cement could be used at the same time for locating the bone cement plug. However, it is a precondition for the use of ultrasonics that all the perturbation elements have substantially the same resonance frequency and hence the same geometry.

In any case, however, the removal of the bone cement is considerably facilitated by using the appropriate method just before the necessary re-operation.

EXAMPLE 1

Polymer matrix: Polymethyl methacrylate with added antibiotics

Perturbation element: Ellipsoid of revolution, produced by revolution of an ellipse with semiaxes of 1 mm and 2 mm about the smaller axis and consisting of the material TiAl$_5$Fe$_{2.5}$ Shock wave:
Pressure range >1 kbar
Pressure rise time <10$^{-7}$ seconds
Half width <10$^{-6}$ seconds

EXAMPLE 2

Polymer matrix: Polymethyl methacrylate with 1% by weight of gentamycin
Perturbation element: Surgical metal thread in the form of a net having a mesh width of about 5 mm and a thread thickness of about 200 μm.

Shock wave:
Pressure range ~1 kbar
Pressure rise time ~10$^{-8}$ seconds
Half width ~10$^{-7}$ seconds

We claim:

1. A method of mechanically disintegrating a matrix of a sold cured polymer containing acoustic perturbation elements having an acoustic resistance differing from that of the polymer by a factor of at least 1.5, said method comprising selectively exciting the perturbation elements by means of sufficiently high intensity acoustic waves, thereby destroying the polymer matrix.

2. A method of claim 1, wherein said polymer is at least one of a polyacrylate and polymethacrylate, and wherein the perturbation elements are present in the polymer in a quantity of about 0.5 to about 20% by volume.

3. A method of claim 2, wherein the acoustic perturbation elements have a thickness of about 0.01 to about 2 mm, and comprise TiAL$_5$Fe$_{2.5}$, CoCrMo, Ta or Al$_2$O$_3$.

4. A method of facilitating the mechanical destruction of a cured solid polymer based on physiologically tolerated polymers comprising at least one of a polyacrylate and a polymethacrylate prepared from a prepolymer and a monomer, which method comprises incorporating into the polymer while it is in the pasty condition, perturbation elements having an acoustic resistance differing from that of the polymer, said perturbation elements comprising TiAl$_5$Fe$_{2.5}$, whereby resultant cured composition can later be disintegrated by selective excitation of said perturbation elements by applying acoustic waves of sufficiently high intensity.

5. A method of claim 4, wherein the acoustic perturbation elements are present in the polymer in a quantity of about 0.5 to about 20% by volume.

6. A method according to claim 4, wherein the acoustic perturbation elements have a thickness of about 0.01 to about 2 mm.

7. A method according to claim 5, wherein the acoustic perturbation elements have a thickness of about 0.01 to about 2 mm.

8. A method according to claim 7, wherein TiAl$_5$Fe$_{2.5}$ is in the form of an ellipsoid of revolution.

9. A method for mechanically disintegrating a solid cured polymer, the latter comprising at least one member from the group consisting of a polyacrylate and a polymethacrylate, said polymer having been prepared from a prepolymer and a monomer and having incorporated therein, while the polymer is in the pasty condition, acoustic perturbation elements having an acoustic resistance different from that of the solid polymer by at least 1.5, said method comprising destroying the matrix of the cured polymer by selective excitation of the perturbation elements by means of acoustic waves which are either extracorporeally generated, focused shock waves, or ultrasonic waves having a frequency tuned to the characteristic frequency of the perturbation elements.

10. A method of claim 9 which comprises employing extracorporeally generated, focused shock waves as the acoustic waves.

11. A method claim 9, which comprises employing as the acoustic waves ultrasonic waves having a frequency tuned to the characteristic frequency of the perturbation elements.

12. A method of claim 9, wherein the acoustic perturbation elements have a thickness of about 0.01 to about 2 mm.

13. A method claim 9, wherein the acoustic perturbation elements are present in a quantity of about 0.5 to about 20% by volume.

14. A method of claim 13, wherein the acoustic perturbation elements have a thickness of about 0.01 to about 2 mm, and comprise TiAl$_5$Fe$_{2.5}$.

15. A method of claim 9 wherein the acoustic perturbation elements comprise TiAl$_5$Fe$_{2.5}$.

16. A method of claim 15, wherein TiAl$_5$Fe$_{2.5}$ is in the form of an ellipsoid of revolution.

* * * * *